US008972235B2

(12) United States Patent
Murphy et al.

(10) Patent No.: US 8,972,235 B2
(45) Date of Patent: Mar. 3, 2015

(54) METHODS AND SYSTEMS FOR SUBTERRANEAN BORE HOLE FRACTURE SIMULATION

(75) Inventors: Robert J. Murphy, Kingwood, TX (US); Dale E. Jamison, Humble, TX (US); Matthew L. Miller, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 363 days.

(21) Appl. No.: 13/401,651

(22) Filed: Feb. 21, 2012

(65) Prior Publication Data

US 2013/0218545 A1    Aug. 22, 2013

(51) Int. Cl.
*G06G 7/48* (2006.01)

(52) U.S. Cl.
USPC ............................................................ 703/10

(58) Field of Classification Search
USPC ............................................................ 703/10
See application file for complete search history.

(56) References Cited

U.S. PATENT DOCUMENTS

| 4,748,849 A * | 6/1988 | Jamison et al. ............... 73/61.64 |
| 5,987,969 A * | 11/1999 | Joseph et al. ................. 73/53.01 |
| 6,584,833 B1 * | 7/2003 | Jamison et al. ............... 73/61.63 |
| 7,721,612 B2 * | 5/2010 | Jamison ....................... 73/863.23 |
| 7,900,504 B2 | 3/2011 | Huynh et al. ................. 73/61.41 |
| 2008/0236891 A1 | 10/2008 | Huynh et al. ................... 175/48 |
| 2009/0217776 A1 * | 9/2009 | Jamison ....................... 73/863.23 |
| 2009/0306898 A1 | 12/2009 | Anschutz et al. ............... 702/11 |

OTHER PUBLICATIONS

PCT/US2013/026419 search report; 2013; 4 pages.*
CPC search notes, 2014, 3 pages.*
"Drilling Fluid Maintenance During Continuous Wellbore Strengthening Treatment," Fred Growcock, Andrea Alba, Mike Miller, Arne Asko and Kyle White, AADE-10-DF-HO-44, 2010, 5 pages, Apr. 2010.

* cited by examiner

*Primary Examiner* — Hugh Jones
(74) *Attorney, Agent, or Firm* — Anthony P. Iannitelli; Baker Botts L.L.P.

(57) ABSTRACT

Apparatus and methods for simulation of bore hole fractures are disclosed. A device for simulating a fracture in a subterranean formation comprises a housing, an inlet for directing a sample fluid to the housing, and a first disk and a second disk positioned within the housing. The second disk is movable relative to the first disk to form an adjustable gap between the first disk and the second disk and the sample fluid flows through the adjustable gap. A common collector receives at least a portion of the sample fluid that flows through at least one of the first disk and the second disk.

14 Claims, 4 Drawing Sheets

METHODS AND SYSTEMS FOR SUBTERRANEAN BORE HOLE FRACTURE SIMULATION

BACKGROUND

The present invention relates to subterranean operations and, more particularly, to apparatus and methods for simulation of bore hole fractures.

Drilling operations play an important role when developing oil, gas or water wells or when mining for minerals and the like. During the drilling operations, a drill bit passes through various layers of earth strata as it descends to a desired depth. Drilling fluids are commonly employed during the drilling operations and perform several important functions including, but not limited to, removing the cuttings from the well to the surface, controlling formation pressures, sealing permeable formations, minimizing formation damage, and cooling and lubricating the drill bit.

When the drill bit passes through porous, fractured or vugular strata such as sand, gravel, shale, limestone and the like, the hydrostatic pressure caused by the vertical column of the drilling fluid exceeds the ability of the surrounding earth formation to support this pressure. Consequently, some drilling fluid is lost to the formation and fails to return to the surface. This loss may be any fraction up to a complete loss of the total circulating drilling fluid volume. This condition is generally known in the art as "Lost Circulation." Failure to control Lost Circulation increases drilling cost and can damage formation production capabilities.

The general practice is to add any number of materials to the drilling fluid which act to reduce or prevent the outward flow of the drilling fluid in a porous and or fractured stratum by sealing pores or cracks, thereby reducing or preventing Lost Circulation. The materials used in this process are commonly referred to as Lost Circulation Materials ("LCM") and may be particles or polymers. Some materials typically used as LCM include, but are not limited to, wood fiber, popped popcorn, straw, bark chips, ground cork, mica, ground and sized minerals and the like.

Further, a technique generally referred to as wellbore strengthening ("WS") may be used to effectively strengthen the walls of a wellbore to prevent fracturing due to overpressure and the subsequent Lost Circulation. This technique takes advantage of inadvertent fractures from normal drilling operations and deliberately induced fractures by sealing and propping the fractures open. Consequently, the wellbore wall is compressed and a higher pressure is required to cause new cracks and further losses of drilling fluid.

In order to optimize the efficiency of drilling operations, LCM may be used in conjunction with Wellbore Strengthening Materials ("WSM"). In some instances, the WSM particles may be larger than the LCM particles. It is desirable to be able to simulate the effect of LCM and/or WSM particles on the formation in order to improve the efficiency of drilling operations and identify the LCM and/or WSM particles best suited for a given formation and performance criteria. Specifically, it is desirable to be able to test a carrier fluid's ability to transport WSM or LCM particles into a new fracture. Further, it is desirable to be able to test the WSM's or LCM's ability to remain in the fracture and prop it open to induce wellbore stress in order to reduce Lost Circulation.

SUMMARY

The present invention relates to subterranean operations and, more particularly, to apparatus and methods for simulation of bore hole fractures.

In one exemplary embodiment, the present disclosure is directed to a device for simulating a fracture in a subterranean formation comprising: a housing; an inlet for directing a sample fluid to the housing; a first disk and a second disk positioned within the housing; wherein the second disk is movable relative to the first disk to form an adjustable gap between the first disk and the second disk; wherein the sample fluid flows through the adjustable gap; a common collector; wherein the common collector receives at least a portion of the sample fluid that flows through at least one of the first disk and the second disk.

In another exemplary embodiment, the present disclosure is directed to a method for simulating subterranean operations comprising: providing a Fracture Simulation Cell having a first disk, a second disk and a common collector; wherein a gap between the first disk and the second disk is adjustable; wherein the common collector provides an outlet for flow of at least a portion of a sample fluid; directing a sample fluid into the Fracture Simulation Cell through an inlet; monitoring at least one of a change in width of the gap between the first disk and the second disk and amount of fluid flow through the common collector; and using at least one of the change in width of the gap between the first disk and the second disk and amount of fluid flow through the common collector to evaluate performance of the sample fluid.

In yet another exemplary embodiment, the present disclosure is directed to a fracture simulation cell comprising: a housing; a first disk and a second disk forming an adjustable gap therebetween; wherein the first disk and the second disk are placed in the housing; a fluid inlet; wherein the fluid inlet directs a sample fluid into the housing; wherein the sample fluid is directed to the adjustable gap; wherein a portion of the sample fluid may flow through at least one of the first disk and the second disk; a fluid outlet; wherein the fluid outlet directs the portion of the sample fluid out of the housing; means for applying a force to at least one of the first disk and the second disk; and means for monitoring movement of at least one of the first disk and the second disk.

The features and advantages of the present invention will be apparent to those skilled in the art from the description of the preferred embodiments which follows when taken in conjunction with the accompanying drawings. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

Figure 4:
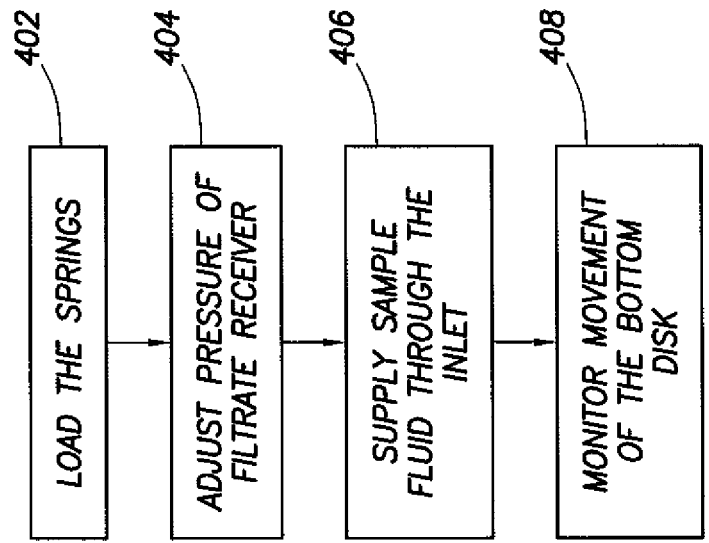
FIG. 4 depicts steps for simulating a fracture in a formation in accordance with an exemplary embodiment of the present invention.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

Illustrative embodiments of the present invention are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory ("RAM"), one or more processing resources such as a central processing unit ("CPU") or hardware or software control logic, ROM, and/or other types of nonvolatile memory. Additional components of the information handling system may include one or more disk drives, one or more network ports for communication with external devices as well as various input and output ("I/O") devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory ("EEPROM"), and/or flash memory; as well as communications media such wires, optical fibers, microwaves, radio waves, and other electromagnetic and/or optical carriers; and/or any combination of the foregoing.

The terms "couple" or "couples," as used herein are intended to mean either an indirect or direct connection. Thus, if a first device couples to a second device, that connection may be through a direct connection, or through an indirect electrical connection via other devices and connections. The term "upstream" as used herein means along a flow path towards the source of the flow, and the term "downstream" as used herein means along a flow path away from the source of the flow. The term "uphole" as used herein means along the drillstring or the hole from the distal end towards the surface, and "downhole" as used herein means along the drillstring or the hole from the surface towards the distal end.

It will be understood that the term "oil well drilling equipment" or "oil well drilling system" is not intended to limit the use of the equipment and processes described with those terms to drilling an oil well. The terms also encompass drilling natural gas wells or hydrocarbon wells in general. Further, such wells can be used for production, monitoring, or injection in relation to the recovery of hydrocarbons or other materials from the subsurface. This could also include geothermal wells intended to provide a source of heat energy instead of hydrocarbons.

The present invention relates to subterranean operations and, more particularly, to apparatus and methods for simulation of bore hole fractures.

Figure 1:
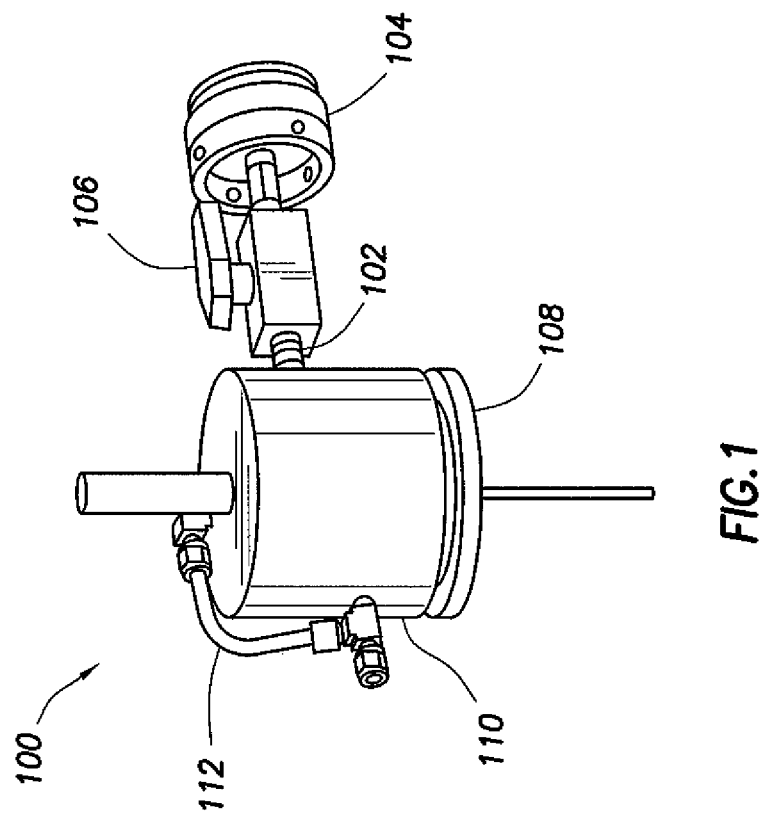
FIG. 1 depicts a Fracture Simulation Cell ("FSC") in accordance with an exemplary embodiment of the present invention.

Turning now to FIG. 1, a Fracture Simulation Cell ("FSC") in accordance with an exemplary embodiment of the present invention is generally denoted with reference numeral 100. The FSC 100 may include a housing with a fluid inlet 102 that supplies fluids containing LCM and/or WSM particles to the FSC 100 from a source 104. In one exemplary embodiment, the source 104 may be a Permeability Plugging Apparatus ("PPA") available from Farm Instrument Company, of Houston, Tex. In one exemplary embodiment, the source 104 may include a pressure or heat generation mechanism that may be used to pressurize and/or heat the sample fluid before it is delivered through the inlet 102. The structure and operation of such heat or pressure generation mechanisms are well known to those of ordinary skill in the art and will therefore not be discussed in detail herein. The flow of the sample fluid from the source 104 through the inlet 102 may be regulated by a valve 106. In one exemplary embodiment, the FSC 100 may be heated to a regulated test temperature before introducing the sample fluid. The FSC 100 housing may further include a cell cap 108, a cell body 110 and filtrate top to bottom connection 112 to ensure pressure consistency on both sides of the filtrate medium.

Figure 2:
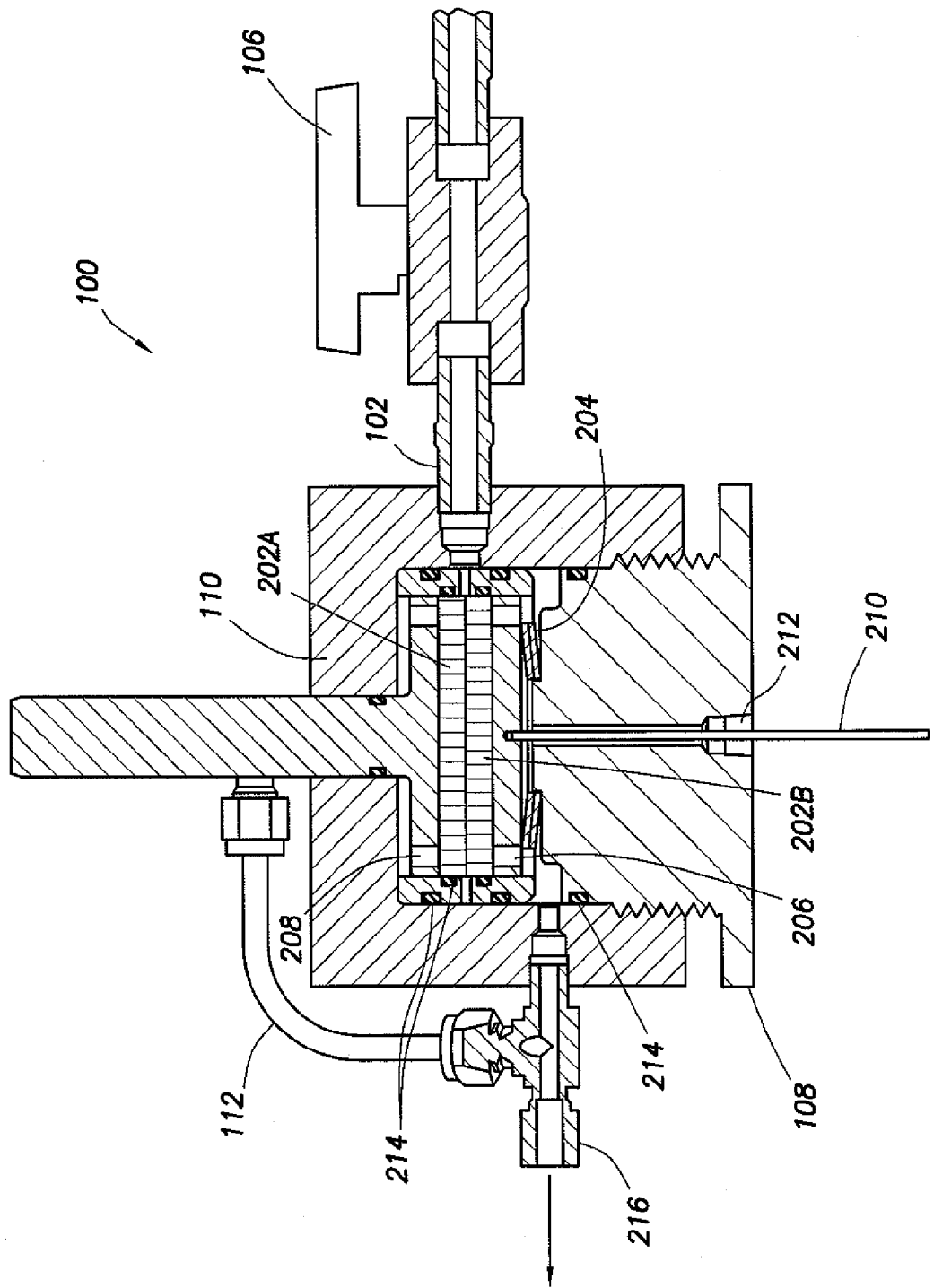
FIG. 2 depicts a cross-sectional view of the FSC of FIG. 1, with a gap simulating a closed fracture.

The structure and operation of the FSC 100 will now be discussed in further detail in conjunction with FIGS. 2 and 3. FIG. 2 depicts a cross-sectional view of the FSC 100 of FIG. 1, with a gap simulating a closed fracture. Inside the FSC 100, disk holders may hold two disks 202A, 202B that simulate the formation. As discussed in more detail below, the disks 202A, 202B may be porous, slotted or solid depending on the nature of the formation that is to be simulated. In accordance with an exemplary embodiment of the present invention, both disks 202A, 202B may be flat, porous, ceramic disks. Further, as would be appreciated by those of ordinary skill in the art, with the benefit of this disclosure, the present disclosure is not limited to any specific disk geometry. Specifically, the disks 202A, 202B may be circular, square or rectangular. It may be desirable for each disk to only be used for a single test in order to obtain the best results. In accordance with an embodiment of the present disclosure, one of the disks may be fixed while the other one may be movable. In the example embodiment illustrated in FIG. 2, the top disk 202A is fixed while the bottom disk 202B is spring loaded.

The force applied by the springs 204 forces the bottom disk 202B towards the top disk 202A in order to press the two disks together. In one embodiment, the springs 204 may be Bellville springs. Accordingly, the top disk 202A and the bottom disk 202B are operable to form an adjustable gap therebetween. The width of the adjustable gap may increase or decrease as the bottom disk 202B moves relative to the top disk 202A. The applied force holding the disks 202A, 202B together simulates the resistance of the subterranean formation to the development of fractures in the formation. Similarly, the stiffness of the springs 204 simulates the stiffness of the formation. In one embodiment, cell cap 108 may be screwed in or out of the FSC 100 in order to load the disks 202A, 202B. Specifically, the amount of force pressing the disks 202A, 202B together may be controlled by the screw on cell cap 108 with the cell cap 108 compressing the springs 204 as it is screwed into the FSC 100. Accordingly, the bottom disk holder 206 which controls the movement of the bottom disk 202B is pressed in place by the springs 204 but is free to move against the springs 204. As the bottom disk holder 206 moves, it will also move the bottom disk 202B relative to the upper disk 202A. The top disk 202A may be held in place by a top disk holder 208. In one embodiment, the top disk holder 208 may be removable but is held stationary against one end of the cell body 110.

The movement of the bottom disk holder 206 and the bottom disk 202B may be detected and monitored by a displacement transducer such as a Linear Variable Differential Transformer ("LVDT"). As would be appreciated by those of ordinary skill in the art, although a LDVT is disclosed herein, other means may be used to monitor the movement of the bottom disk holder 206. For instance, in other embodiments, laser or capacitive displacement sensors may be used to monitor movement of the bottom disk holder 206. In one embodiment, as shown in FIG. 2, the displacement transducer (not shown) may be connected to a rod 210 that is coupled to the bottom disk holder 206 and/or the bottom disk 202B and extends out from the FSC 100 through a seal 212. In another exemplary embodiment (not shown), the displacement transducer may be placed within the FSC 100 and directly connected to the disk holder 206 or the disk 202B.

One or more seals 214 are placed around the disk holders 206, 208 and isolate the cavities between and around the disks 202A, 202B. Additional seals may be provided around the disk holder shafts and the cell cap 108 to prevent leakage of fluids from the FSC 100. Passages in the disk holders 206, 208 allow fluid flowing through the disks 202A, 202B to be collected by a common collector 216. The common collector 216 may be pressurized by means of a receiver (not shown) to simulate the pressurized fluid in the spaces within a subterranean formation's pores.

In operation, a sample fluid flows through the inlet 102 into the FSC 100. As the sample fluid flows into the FSC 100, a portion of the sample fluid will enter the adjustable gap between the disks 202A, 202B. In embodiments with disks 202A, 202B having holes, slots, or pores, at least a portion of the sample fluid may pass through the holes, slots, or pores of the disks 202A, 202B to the common collector 216. In one embodiment, the fluid that passes through the top disk 202A and the bottom disk 202B may be collected and measured separately. In certain embodiments, the pressure of the fluid that passes through the top disk 202A and the bottom disk 202B may be maintained separately by separate collectors and receivers (not shown).

In one embodiment, before performing a test using the FSC 100, the cavities and pores inside the FSC 100 may be prefilled with a simulated formation pore fluid to more accurately represent actual conditions of the formation. When performing the test, the valve 106 may be opened and the sample fluid begins to flow from the source 104 towards the FSC 100 through the inlet 102. Once the pressure of the sample fluid exceeds the simulated pore pressure, some of the sample fluid will flow through the porous disks 202A, 202B through the common collector 216 and into the receiver (not shown).

The amount of sample fluid that flows through the porous disks can be determined by measuring the displaced simulated formation pore fluid that collects in the receiver (not shown) through the common collector 216. The volume of fluid that passes through the porous disks 202A, 202B is an indication of the sealing efficiency of the sample fluid. If the disks 202A, 202B are sealed by the LCM/WSM and the pressure of the sample fluid is raised high enough, the moveable disk holder 206 is forced against the springs 204 with enough force to overcome the preload force of the springs 204. As a result, the bottom disk holder 206 moves, opening a gap or simulated fracture between the two disks 202A, 202B. A portion of the sample fluid, the filtrate, flows through the gap, through the disks 202A, 202B, and out of the housing to the common collector 216. Typically, the filtrate is stripped of many solids initially present in the sample.

As discussed above, in certain embodiments, the disks 202A, 202B may be solid disks simulating impermeable formations. When using solid disks, no fluid may flow through the disks 202A, 202B and to the common collector 216. Further, as would be appreciated by those of ordinary skill in the art, with the benefit of this disclosure, when a porous formation is simulated using porous disks 202A, 202B flow of the sample fluid from the adjustable gap between the disks 202A, 202B to the common collector 216 may leave a filter cake behind that may plug or partially plug the pores in the disks 202A, 202B. In order to accurately simulate a desirable formation, the disks 202A, 202B may be selected to have pore throat sizes similar to the size of the pores in the desirable formation being simulated.

Figure 3:
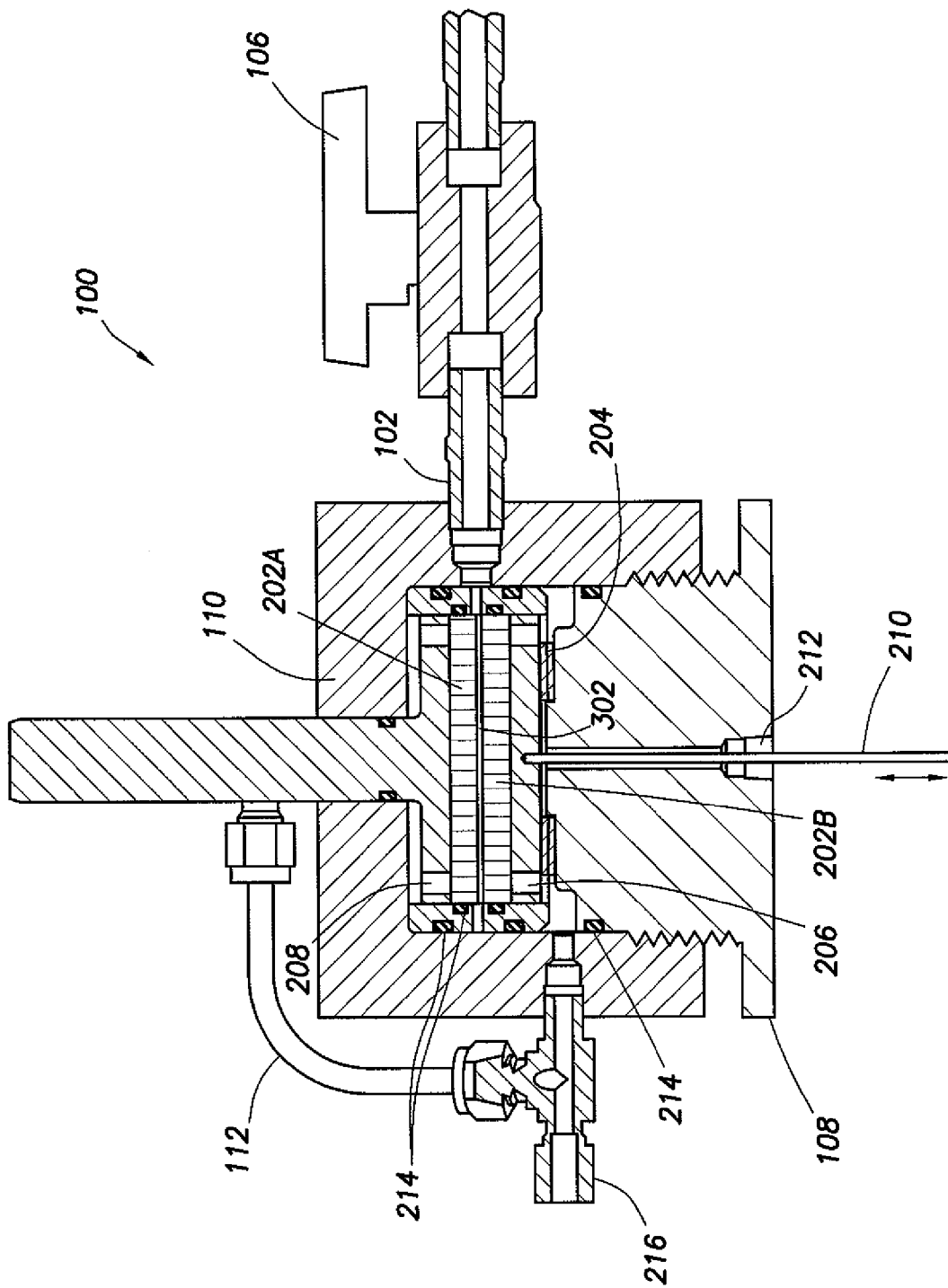
FIG. 3 depicts a cross-sectional view of the FSC of FIGS. 1 and 2, with a gap simulating an open fracture.

FIG. 3 depicts a cross-sectional view of the FSC 100 of FIGS. 1 and 2, with an adjustable gap simulating an open fracture 302 between the disks 202A, 202B. If the pressure of the sample fluid is subsequently lowered, the springs 204 try to reclose this gap or simulated fracture between the porous disks 202A, 202B. However, the LCM/WSM left in the fracture 302 resists the re-closure of the fracture 302. How far the fracture 302 opens and the degree to which the fracture 302 is held open on depressurization is determined by examining the displacement of the moveable disk 202B which may be measured by the displacement transducer. In one embodiment, the test cycle may be repeated to determine if more LCM/WSM may be deposited in the fracture 302.

FIG. 4 depicts steps for simulating a fracture in a formation in accordance with an exemplary embodiment of the present invention. At step 402, the springs 204 are loaded. Specifically, an initial normal stress may be imposed by compressing the springs 204 to some preload value representing the formation strength. In one exemplary embodiment, the springs 204 may be loaded by tightening the cell cap 108. Further, the stiffness of the springs 204 may be selected so that it simulates the formation stiffness. Next, at step 404, the pressure of the filtrate receiver through the common inlet 216 may be adjusted. The pressure in the filtrate receiver simulates the formation pore pressure. At step 406, a sample fluid may be directed to the FSC 100 through the inlet 102. Specifically, the valve 106 may be opened permitting flow of the sample fluid from the source 104 to the FSC 100 through the inlet 102. For instance, if the disks 202A, 202B are porous and the sample fluid includes LCM, then the LCM may seal the pores in the disks which represent the pores of the simulated formation. Once the pressure of the sample fluid is high enough, the disks 202A, 202B are forced apart, creating a gap 302 which simulates a fracture. The changes in the gap between the disks 202A, 202B may be used to evaluate the performance of the sample fluid. Specifically, the changes in the gap width may be used to determine the effectiveness of the sample fluid for its intended purpose when utilized in conjunction with a fracture in a subterranean formation as simulated by the FSC. For example, an LCM that is easily crushed may allow the crack to mostly close when the sample pressure is lowered. Accordingly, an LCM that is easily crushed would offer little value as a WSM.

Because in the exemplary embodiment of FIGS. 1-3 the upper disk 202A is fixed, the changes in the fracture width may be monitored by monitoring the movement of bottom disk 202B. Accordingly, the motion of the bottom disk 202B is sensed by a displacement transducer that may be connected to the protruding rod 210 or positioned within the FSC 100. When the pressure of the sample fluid is reduced, the springs 204 try to close the fracture 302 by pushing the bottom disk 202B up towards the upper disk 202A. The closing force at any position may be calculated from the spring constant of the springs 204, receiver and sample pressures, and the measured bottom disk 202B displacement.

In accordance with an exemplary embodiment of the present invention, the FSC 100 may be heated to a desired temperature to simulate the formation temperature. In one embodiment, a custom heat jacket may be used to heat the FSC 100.

As would be appreciated by those of ordinary skill in the art, the configuration of the disks may be varied depending on the type of formation and fracture being simulated. For instance, the porous disks 202 may be replaced with non-porous disks in order to simulate non-porous formations. Other disk configurations may similarly be utilized to simulate different, desirable formation conditions. For instance, the disks 202 may be two permeable disks, two impermeable disks, two slotted disks (e.g., simulating a large existing crack in the formation), combination of permeable and slotted disks, combination of disks with different surface textures or combinations of permeable, impermeable and slotted disks. Specifically, in certain embodiments, the surface texture of the disks 202 on the surfaces forming the adjustable gap may be altered to simulate different types of cracks in various formations. Therefore, in certain embodiments, it may be desirable to control the surface texture of the disks 202A, 202B in a repeatable manner in order to provide a more accurate simulation of a particular formation. In one exemplary embodiment, a slightly conical impermeable disk may be combined with a permeable disk or a slotted disk. In another exemplary embodiment, tilted permeable or impermeable disk combinations may be used to simulate a crack with a taper. In yet another exemplary embodiment, permeable or impermeable disks with repeatable irregular or regular recessed cavities may be utilized to simulate fractures in vugular formations. In another exemplary embodiment, the disks 202 may be pre-spaced so that they have an initial gap therebetween.

Figure 5:
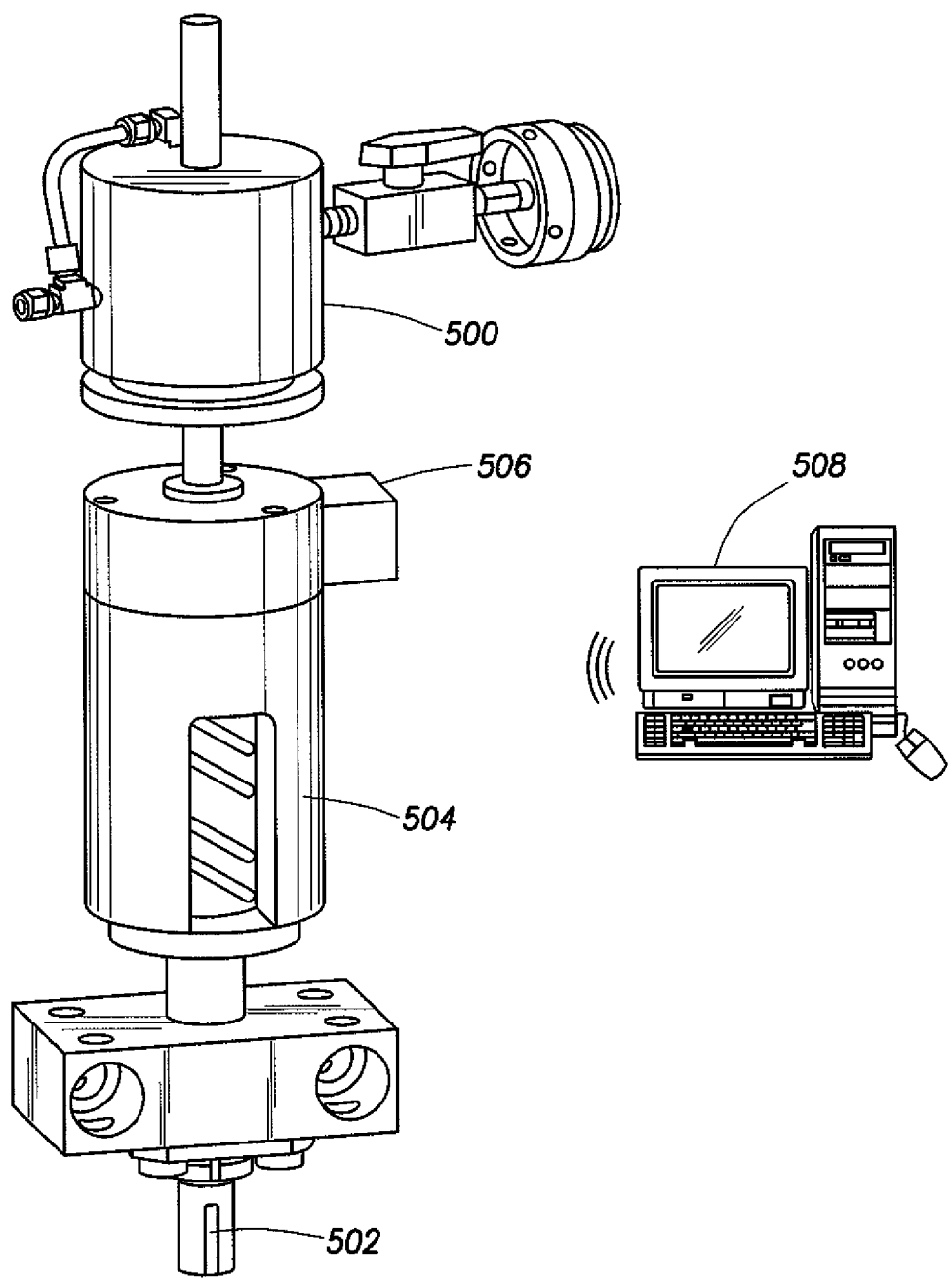
FIG. 5 depicts a FSC in accordance with a second embodiment of the present disclosure.

FIG. 5 depicts a FSC in accordance with a second embodiment of the present disclosure denoted generally with reference numeral 500. In accordance with the second embodiment of the present disclosure, a mechanical or a hydrolytic actuator may be used to exert force and control the position of the movable disk holder 206 (and the movable disk 202B). Specifically, the movable disk holder 206 may be coupled to a motor drive connection 502 through a ball screw 504. As would be appreciated by those of ordinary skill in the art, with the benefit of this disclosure, the ball screw 504 may translate the rotational motion of the motor drive connection 502 into linear motion. In one embodiment, the motor drive connection 502 may be a Servo Motor Drive Connection. The linear motion generated by the ball screw 504 may then be used to move the movable disk holder 206 and the disk 202B and control the gap between the disks 202A, 202B. A force transducer 506 may be used to monitor the force exerted on the movable disk holder 206 and/or the movable disk 202B. The operation of the remaining portions of the FSC 500 are the same as that of the FSC 100 discussed above, and will therefore not be discussed in detail.

As would be appreciated by those of ordinary skill in the art, with the benefit of this disclosure, replacing the springs 204 with an actuator permits a more precise control and monitoring of the simulated fracture width, opening and closing rate, applied preload force and the closure force.

In one embodiment, the motor that drives the motor drive connection 502 and controls the force exerted on the movable disk holder 206 may be controlled by an information handling system 508. The information handling system may be communicatively coupled to the FSC 500 through a wired or wireless communication system. Use of such communication systems is well known to those of ordinary skill in the art and will therefore not be discussed in detail herein. In one embodiment, the information handling system 508 may regulate system parameters such as the force exerted on the movable disk holder 206 and the bottom disk 202B, the temperature of the FSC 100, 500, the temperature of the sample fluid, or other system criteria discussed in detail above in order to simulate desired wellbore conditions. In one embodiment, the information handling system 508 may include a user interface, allowing the user to specify the different system parameters. Moreover, the information handling system 508 may monitor the movement of the moveable disk holder 206 and the bottom disk 202B in response to the sample fluid flow through the FSC 100, 500. By monitoring the movement of the bottom disk holder 206 and the disk 202B, the information handling system may keep track of the changes in the width of the adjustable gap between the disks 202A, 202B. In one embodiment, the data reflecting the movement of the bottom disk 202B and/or the gap between the two disks 202A, 202B may be stored by the information handling system in a computer-readable media and be used to evaluate the performance of a sample fluid over a set time period.

As would be appreciated by those of ordinary skill in the art, with the benefit of this disclosure, an FSC in accordance with embodiments of the present disclosure may have a number of applications. For instance, in one embodiment, the FSC may be modified to permit introduction of multiple fluids in order to simulate wellbore treatment processes. Specifically, the inlet 102 may be replaced by a plurality of inlets each supplying a different fluid to the FSC. In another exemplary embodiment, the FSC may have a single inlet with a valve used to select which of the plurality of desirable fluids flows through the inlet. Each of the fluids may be conditioned to a different temperature and pressure if desirable to simulate specific conditions.

Moreover, in addition to testing LCM and WSM carrying fluids, the FSC may be utilized for testing and characterization of chemical treatments used in subterranean operations such as, for example, cement and polymers that harden in place. Specifically, in certain subterranean applications chemical treatment may be used to replace and/or compliment the use of LCM/WSM materials. For instance, once desired cracks are created in a formation, chemical treatments may be used to prop the cracks open. It is therefore desirable to simulate the interaction of chemical treatments with the formation. Accordingly, the sample fluid directed to the FSC may be a chemical treatment fluid. The FSC 100, 500 may then be used to analyze the performance of the chemical treatment using similar methods as those described above.

In accordance with another exemplary embodiment of the present invention, the FSC may be modified to apply shear to the fracture face by flowing one or more fluids across the fracture face by means of a circulation loop and pump and an outlet port for the sample roughly opposite the sample inlet port (not shown). Once introduced, the sample would flow between the disk pair, out the sample outlet port, through the pump which induces and controls the flow rate, and back to the FSC sample inlet port.

In some embodiments, the FSC may be utilized to simulate swabbing situations to test for unplugging. Specifically, when performing drilling operations, the pressure in the wellbore may be reduced by moving pipe, wireline tools, seals and other equipment up the wellbore. If the pressure is sufficiently reduced, fluids may flow from the formation into the wellbore through the fractures and towards the surface. This is referred to as swabbing. Swabbing is generally undesirable as it may lead to kicks and/or wellbore stability problems. Accordingly, the FSC may be utilized to simulate swabbing situations by first forming an LCM plug in a simulated fracture between disks 202A, 202B, regulating the force applied to the movable disk holder 206, and manipulating the pressure at the inlet 102 and the common collector 216 to simulate swabbing under specific wellbore conditions.

In one exemplary embodiment, FSCs in accordance with the present disclosure may be utilized to simulate long formation cracks. Specifically, a plurality of disk pairs may be arranged so that the sample fluid flows through them in sequence to simulate long formation cracks. In one embodiment, two or more FSCs may be connected in series by adding a port to each cell opposite the sample inlet port to allow the sample fluid to flow from one FSC to the next FSC in sequence to analyze the performance of the sample fluid at different positions along the simulated long formation crack.

Finally, in another exemplary embodiment, the FSC may be utilized to test long term stability or degradability of filter cakes and plugs formed in the apparatus. For instance, once LCM materials are introduced into the FSC the device may be held at a desired temperature to simulate field conditions. Measurements may then be obtained over time to monitor the performance of the filter cakes and plugs formed in the simulated crack. For instance, a stable WSM would keep the simulated crack open.

As would be appreciated by those of ordinary skill in the art, with the benefit of this disclosure, although the present application discloses an arrangement with a movable bottom disk and a fixed top disk, the present disclosure is not limited to that arrangement. For instance, in another exemplary embodiment, the top disk may be movable while the bottom disk is fixed. In yet another exemplary embodiment, the top disk and the bottom disk may be both movable and may be used in conjunction to create the adjustable gap.

Accordingly, the apparatus and methods disclosed herein incorporate a simulated fracture that can be opened and closed under simulated wellbore conditions and measure parameters that can be used to predict wellbore performance.

Therefore, the present invention is well-adapted to carry out the objects and attain the ends and advantages mentioned as well as those which are inherent therein. While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects. The terms in the claims have their plain, ordinary meaning unless otherwise explicitly and clearly defined by the patentee.

What is claimed is:

1. A device for simulating a fracture in a subterranean formation comprising:
    a housing;
    an inlet for directing a sample fluid to the housing;
    a first disk and a second disk positioned within the housing;
        wherein the second disk is movable relative to the first disk to form an adjustable gap between the first disk and the second disk;
        wherein the sample fluid flows through the adjustable gap;
    a common collector;
        wherein the common collector receives at least a portion of the sample fluid that flows through at least one of the first disk and the second disk;
    at least one of a spring and an actuator, wherein the at least one of the spring and the actuator applies a force to the second disk and wherein the force directs the second disk towards the first disk;
    a displacement transducer coupled to the second disk, wherein the displacement transducer detects a movement of the second disk relative to the first disk; and
    a force transducer, wherein the force transducer monitors a force exerted on the second disk.

2. The device of claim 1, wherein the first disk is immovable relative to the housing.

3. The device of claim 1, wherein a spring applies the force to the second disk; and a cell cap coupled to the housing, wherein the cell cap compresses the spring.

4. The device of claim 1, further comprising an information handling system, wherein the information handling system at least one of regulates a force applied to the second disk and monitors movement of the second disk.

5. The device of claim 1, wherein at least one of the first disk and the second disk is selected from a group consisting of a porous disk, a slotted disk and a solid disk.

6. A method for simulating subterranean operations comprising:
    providing a Fracture Simulation Cell having a first disk, a second disk and a common collector;
        wherein the second disk is movable relative to the first disk forming an adjustable gap between the first disk and the second disk;
        wherein the gap between the first disk and the second disk is adjusted using a mechanism selected from the group consisting of at least one of a spring and an actuator;
        wherein the at least one of the spring and the actuator applies a force to the second disk and the force directs the second disk towards the first disk;
        wherein the common collector provides an outlet for flow of at least a portion of a sample fluid;
    directing a sample fluid into the Fracture Simulation Cell through an inlet;
    monitoring of a change in width of the gap between the first disk and the second disk;
    wherein monitoring the change in width of the gap between the first disk and the second disk comprises coupling the second disk to a displacement transducer to monitor movement;
    monitoring a force exerted on the second disk, wherein a force transducer monitors the force exerted on the second disk; and using the change in width of the gap between the first disk and the second disk and amount of force exerted on the second disk to evaluate performance of the sample fluid.

7. The method of claim 6, wherein the common collector is pressurized before directing the sample fluid into the Fracture Simulation Cell, wherein the pressurization of the common collector simulates pressure of fluids in spaces within a subterranean formation.

8. The method of claim 7, further comprising reducing pressure of the sample fluid and monitoring fluid flow from the common collector to the inlet.

9. The method of claim 6, wherein the sample fluid comprises material selected from a group consisting of Loss Circulation Materials, Wellbore Strengthening Materials, and chemical treatments.

10. The method of claim 6, further comprising heating at least one of the sample fluid and the Fracture Simulation Cell.

11. The method of claim 6, further comprising monitoring a force exerted on at least one of the first disk and the second disk.

12. The method of claim 6, wherein directing a sample fluid into the Fracture Simulation Cell comprises directing a plurality of fluids to the Fracture Simulation Cell.

13. A fracture simulation cell comprising:
a housing;
a first disk and a second disk,
wherein the second disk is movable relative to the first disk, forming an adjustable gap therebetween;
wherein the first disk and the second disk are placed in the housing;
at least one of a spring and an actuator, wherein the at least one of the spring and the actuator applies a force to the second disk and wherein the force directs the second disk towards the first disk;
a fluid inlet;
wherein the fluid inlet directs a sample fluid into the housing;
wherein the sample fluid is directed to the adjustable gap;
wherein a portion of the sample fluid may flow through at least one of the first disk and the second disk;
a fluid outlet;
wherein the fluid outlet directs the portion of the sample fluid out of the housing;
means for applying a force to at least one of the first disk and the second disk;
a displacement transducer coupled to the second disk, wherein the displacement transducer monitors a movement of the second disk relative to the first disk; and
a force transducer, wherein the force transducer monitors a force exerted on the second disk.

14. The fracture simulation cell of claim 13, wherein at least one of the first disk and the second disk is selected from a group consisting of a porous disk, a slotted disk and a solid disk.

* * * * *